US008895732B2

(12) United States Patent
Helmreich et al.

(10) Patent No.: US 8,895,732 B2
(45) Date of Patent: Nov. 25, 2014

(54) PROCESS FOR THE SEPARATION OF ENANTIOMERS OF 3,6-DIHYDRO-1,3,5-TRIAZINE DERIVATIVES

(75) Inventors: Matthias Helmreich, Darmstadt (DE); Claus Peter Niesert, Seeheim-Jugenheim (DE); Michael Schulte, Bischofsheim (DE); Wolfgang Lindner, Klosterneuburg (AT); Michael Laemmerhofer, Vienna (AT); Christian Hoffmann, Bayreuth (DE)

(73) Assignee: Merck Patent GmbH, Darmstadt (DE)

( * ) Notice: Subject to any disclaimer, the term of this patent is extended or adjusted under 35 U.S.C. 154(b) by 290 days.

(21) Appl. No.: 13/258,629

(22) PCT Filed: Feb. 26, 2010

(86) PCT No.: PCT/EP2010/001219
§ 371 (c)(1),
(2), (4) Date: Sep. 22, 2011

(87) PCT Pub. No.: WO2010/108583
PCT Pub. Date: Sep. 30, 2010

(65) Prior Publication Data
US 2012/0016121 A1 Jan. 19, 2012

(30) Foreign Application Priority Data
Mar. 25, 2009 (DE) .......................... 10 2009 014 898

(51) Int. Cl.
*C07D 251/10* (2006.01)

(52) U.S. Cl.
CPC .................................... *C07D 251/10* (2013.01)
USPC ............ 544/204; 544/206; 544/208; 544/209

(58) Field of Classification Search
USPC .................................. 544/204, 206, 208, 209
See application file for complete search history.

(56) References Cited

U.S. PATENT DOCUMENTS

| 7,501,511 B2 * | 3/2009 | Moinet et al. ................. 544/206 |
| 2005/0131087 A1 | 6/2005 | Lindner et al. |
| 2006/0223803 A1 | 10/2006 | Moinet et al. |

FOREIGN PATENT DOCUMENTS

| WO | WO 03/068397 A1 | 8/2003 |
| WO | WO 2004/089917 A2 | 10/2004 |

OTHER PUBLICATIONS

International Search Report of PCT/EP2010/001219 (Jun. 1, 2010).

* cited by examiner

*Primary Examiner* — Venkataraman Balasubramanian
(74) *Attorney, Agent, or Firm* — Millen, White, Zelano & Branigan, P.C.

(57) ABSTRACT

Method for the chromatographic separation of compounds of the formula (I), in which $R^1$, $R^2$, $R^3$, $R^4$, $R^5$, $R^6$ have the meanings indicated in Claim 1, and acid-addition salts thereof, characterized in that the separation is carried out on a chiral ion-exchanger material.

3 Claims, 8 Drawing Sheets

PROCESS FOR THE SEPARATION OF ENANTIOMERS OF 3,6-DIHYDRO-1,3,5-TRIAZINE DERIVATIVES

The invention relates to a method for the chromatographic separation of racemic and non-racemic mixtures of the enantiomers of the compounds of the formula I

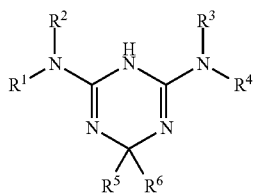

I in which
R$^1$, R$^2$ each, independently of one another, denote H or A,
R$^3$, R$^4$ each, independently of one another, denote H, A, alkenyl having 2-10 C atoms, alkynyl having 2-10 C atoms, Ar or Het,
R$^5$ and R$^6$ together also denote alkylene having 2, 3, 4 or 5 C atoms,
R$^5$, R$^6$ each, independently of one another, denote H, A, (CH$_2$)$_n$Ar, (CH$_2$)$_m$OAr, (CH$_2$)$_m$OA or (CH$_2$)$_m$OH,
R$^5$ and R$^6$ together also denote alkylene having 2, 3, 4 or 5 C atoms, in which one CH$_2$ group may be replaced by O, NH or NA and/or in which 1H atom may be replaced by OH,
Ar denotes phenyl, naphthyl or biphenyl, each of which is unsubstituted or mono-, di- or trisubstituted by Hal, A, OA, OH, COOH, CODA, CN, NH$_2$, NHA, NA$_2$, SO$_2$A and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, OH, OA, NH$_2$, (CH$_2$)$_n$Ar, NHA, NA$_2$, COOH, CODA and/or =O (carbonyl oxygen),
A denotes unbranched or branched alkyl having 1-10 C atoms, in which 1-7 H atoms may be replaced by F, or cyclic alkyl having 3-7 C atoms,
Hal denotes F, Cl, Br or I,
m denotes 1, 2, 3, 4, 5 or 6,
n denotes 0, 1 or 2,
and acid-addition salts thereof,
characterised in that the separation is carried out on a chiral ion-exchanger material.

The compounds of the formula I are useful in the treatment of diseases associated with insulin resistance syndrome.

A method for resolving racemates of compounds of the formula I by salt formation and separation of the diastereomeric salts is known from WO 2004/098817.

Surprisingly, investigations in the course of the separation of dihydro-1,3,5-triazinamine derivatives showed that the compounds of the formula I can be obtained in considerably higher yield and in greater enantiomeric excess compared with the prior art.

In particular, the compound 4-amino-3,6-dihydro-2-dimethylamino-6-methyl-1,3,5-triazine is prepared by the method according to the invention.

In contrast to the prior art known to date on the analytical separation of enantiomers by means of supercritical HPLC on chiral phases, which is described in WO 2004/098817, an analytical method for the determination of the two enantiomers by means of standard HPLC has, surprisingly, nevertheless been found. This has the advantage that special equipment is no longer necessary for the separation.

The mobile phase typically consists of a polar solvent, such as, for example, methanol, ethanol, water, isopropanol, and an acidic or basic buffer salt. The mobile phase typically comprises 0.01% to 2% of this acidic or basic buffer salt.

The stationary phase selected is typically a chiral support from the group of the oligosaccharides, polysaccharides, or macrocyclic glycoproteins bonded to silica gel. Supports of this type are commercially available under the trade names Chiralcel® from Daicel, Chirose® from Chiralsep and Chirobiotic® from Astec.

Above and below, the radicals R$^1$, R$^2$, R$^3$, R$^4$, R$^5$, R$^6$ have the meanings indicated in the case of the formula I, unless expressly indicated otherwise.

Formula I also encompasses the optically active forms (stereoisomers), such as the enantiomers.

Metformin as preferred starting material has the structure

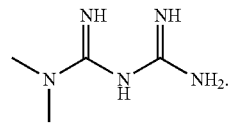

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A furthermore preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A very particularly preferably denotes methyl.

Cyclic alkyl(cycloalkyl) preferably denotes cyclopropyl, cyclobutyl, cylopentyl, cyclohexyl or cycloheptyl.

Alkenyl has 2, 3, 4, 5 or 6 C atoms and preferably denotes vinyl, propenyl or hexenyl.

Alkynyl has 2, 3, 4, 5 or 6 C atoms and preferably denotes C≡CH or C≡C—CH$_3$.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-(N-methylaminocarbonyl)-phenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N-ethylamino)-phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonyl)phenyl, o-, m- or p-cyanophenyl, o-, m- or p-carboxyphenyl, o-, m- or p-methoxycarbonylphenyl, o-, m- or p-acetylphenyl further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-amino-4-chloro-, 2-amino-3-chloro-, 2-amino-4-chloro-, 2-amino-5-chloro- or 2-amino-6-chlorophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-fluoro-4-methoxyphenyl, 3-amino-6-methylphenyl or 2,5-dimethyl-4-chlorophenyl.

Ar particularly preferably denotes phenyl, hydroxyphenyl or methoxyphenyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated.

Irrespective of further substitutions, Het may thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl or benzo-2,1,3-thiadiazolyl, each of which is unsubstituted or mono-, di- or trisubstituted by A, COOA, Hal and/or =O (carbonyl oxygen).

$R^1$, $R^2$ preferably denote A.
$R^3$, $R^4$ preferably denote H.
$R^5$ preferably denotes H.
$R^6$ preferably denotes A.
Very particularly preferably,
$R^1$, $R^2$ denote methyl,
$R^3$, $R^4$ denote H,
$R^5$ denotes H,
$R^6$ denotes methyl.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, for example picrates, can be used for the isolation and/or purification of the compounds of the formula I.

In principle, enantiomers can be separated on chiral sorbents. A large number of chiral sorbents is known to the person skilled in the art, for example those based on cellulose derivatives, cyclodextrins, or poly(meth)-acrylamide derivatives having an optically active side chain. Chiral sorbents of this type and the use thereof are disclosed, for example, in "Recent developments in liquid chromatographic enantioseparation. M. Lämmer-hofer, W. Lindner in *Handbook of analytical separations* (Vol. 1): *Separation methods in drug synthesis and purification* (K. Valko, Editor), Elsevier, NL, 2000" or in "Enantiomer Separation. M. Lämmerhofer, N. M. Maier, W. Lindner, in: L. R. Snyder, J. J. Kirkland, and J. W. Dolan (Editors), Introduction to Modern Liquid Chromatography, 3rd edition, John Wiley, Hoboken, N.J., USA, 2009".

Surprisingly, however, it has been found that separation of this class of compounds is also possible on an ion-exchanger material.

Exchange materials of this type for enantioselective separation are described, for example, in WO 03/068397 A1.

Characteristics of the enantioselective ion-exchanger materials which solve the problem according to the invention are described below. The ion-exchanger materials used are built up essentially from an i.) anionic or zwitterionic chiral selector, ii.) a support, and iii) a linker, which connects the chiral selector to the support.

The anionic or zwitterionic chiral selector consists of a chiral framework in enantiomerically pure form having at least one acid function, where the acid function is a a carboxylic, sulfonic, sulfinic, phosphoric, phosphonic or phosphinic acid group. This acid group causes the ionic interaction of the chiral selector or ion-exchange material with the compound of the formula I to be separated. The chiral framework contains at least one chiral element from the group of the centres of chirality, chiral axes, chiral planes and chiral helices and is employed in the form of a defined stereoisomer, where the stereochemical purity of this chiral framework should be as high as possible. The chiral selectors are often built up by the linking of a plurality of centres of chirality, which causes a number of well-defined stereoisomers. The chiral element and the combination of the chiral elements of the framework provide the basis for the chiral recognition ability of the enantioselective ion-exchange material. The chiral ion-exchange framework is preferably a low-molecular-weight compound from the group of the natural or synthetic, cyclic or non-cyclic amino acids, hydroxycarboxylic acids, aminosulfonic acids, aminophosphonic acids, aminophosphinic acids, aminosulfinic acids, hydroxyphosphonic acids, hydroxyphosphinic acids, ketosulfonic acids, tartaric acid, camphorsulfonic acid, mandelic acid, sulfated compounds, peptides or sulfopeptides.

The low-molecular-weight ion-exchange selector may also be an amphoteric compound, which carries at least one charged acidic group under the conditions used. Further typical structural elements which distinguish a successful chiral ion-exchange selector for the enantiomeric separation of the target compounds of the formula I are additional hydrogen donor-acceptor groups (such as amides, carbamates, sulfonamides, urea, carbonyl, semicarbazide, hydrazide, or sulfonimide groups or other hydrogen donor-acceptor systems), pi-pi interaction points (i.e. aromatic groups, preferably having electron-withdrawing or electron-donating functional groups), and optionally bulky groups for steric interactions or van der Waal's interaction. These secondary interaction forces are frequently stereoselectively pronounced and cause the different affinity of the two enantiomers of the target compound to be separated.

For most applications, the chiral ion-exchange selector must be immobilised on a solid or optionally liquid support. Suitable supports are inorganic, organic, or mixed inorganic/organic hybrid materials. The support can originate from the group of particulate or monolithic materials, which includes silica gel ($SiO_2$), alumina ($Al_2O_3$), zirconia ($ZrO_2$), titania ($TiO_2$), other sol-gel materials, organic/inorganic carbon/silicon-containing hybrid materials, optionally crosslinked polysiloxanes, optionally crosslinked organic polymers from the group of the poly(meth)acrylates, poly(meth)acrylamides, polystyrenes, "ring-opening methathesis" polymers, mixed forms of these organic polymers, polysaccharides, agarose and ceramic materials. The supports are preferably porous materials having an average pore width of 60 Å to 1000 Å, but may also be non-porous or superporous having pore widths greater than 1000 Å.

The linker has the function of anchoring the selector to the surface of the support and rendering the selector accessible to interaction with the target compound. Both the length and also the chemical structure of the linker are variable, since this is generally only indirectly involved in the chiral recognition and separation. In some cases, no linker is necessary, namely when the ion-exchange selector in monomeric or polymeric form is coated directly onto the surface of the support. All conventional solid-phase linker concepts can be used. Typical immobilisation strategies use a bifunctional linker, which is firstly anchored to the support by means of a functional group and, in the second step, is chemically reacted with the chiral ion-exchange selector via a reactive anchor group of the modified support and is thus immobilised on the support. Ion-exchange selectors having a double bond can thus be covalently bonded, for example, to thiol-modified silica gel.

Besides the subsequent brush-like anchoring to the surface of the support, concepts such as graft polymerisation and similar polymeric anchoring strategies are also conceivable. The chiral ion-exchange selector can also be embedded in the support by in-situ copolymerisation and thus anchored.

The resultant coverage densities are preferably between 100 and 1000 µmol of ion-exchange selector/g of stationary phase.

The eluent used is preferably
i) an organic solvent from the group methanol, ethanol, propanol, acetonitrile, THF, dioxane, ethyl acetate, chloroform, dichloromethane, tert-butyl methyl ether, hexane, heptane, or a binary, ternary, quaternary mixture of these solvents with addition of co- and counterions or also without ionogenic additives,
ii) an aqueous medium with or without addition of buffers and with or without miscible polar organic solvents from the group as specified under i.),
iii) supercritical or subcritical $CO_2$ with or without an organic solvent as specified under i.), with addition of co- and counterions or also without ionogenic additives.

The additives used are preferably volatile. The elution of the components is preferably effected in isocratic mode, but can also be carried out in gradient-elution mode.

The separation can be carried out in a conventional zone-elution chromatography method with discontinuous sample application and continuous elution, in batch mode, by recycling chromatography, or by a continuous chromatography method (such as simulated moving bed SMB technology).

The chromatographic separation can be effected by means of HPLC, UPLC, SFC technology.

The method according to the invention gives yields of almost 50% with an ee>98%, based on the racemic mixture to be separated that is employed.

EXAMPLE 1

For the method according to the invention, the chiral ion-exchanger material having the following chemical structure, based on silica gel as support material, can be employed, for example. The type of counterion X— at the cation exchanger site depends on the type of buffer salt in the mobile phase.

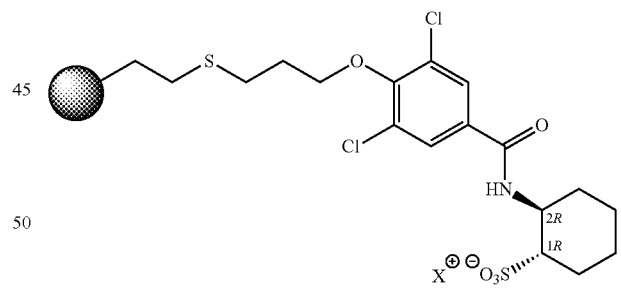

Using this ion-exchanger material, the following chromatographic separation of the racemate of the compound of the formula I, in which
$R^1$, $R^2$ denote methyl,
$R^3$, $R^4$ denote H,
$R^5$ denotes H,
$R^6$ denotes methyl,
can be achieved.

Figure 1:
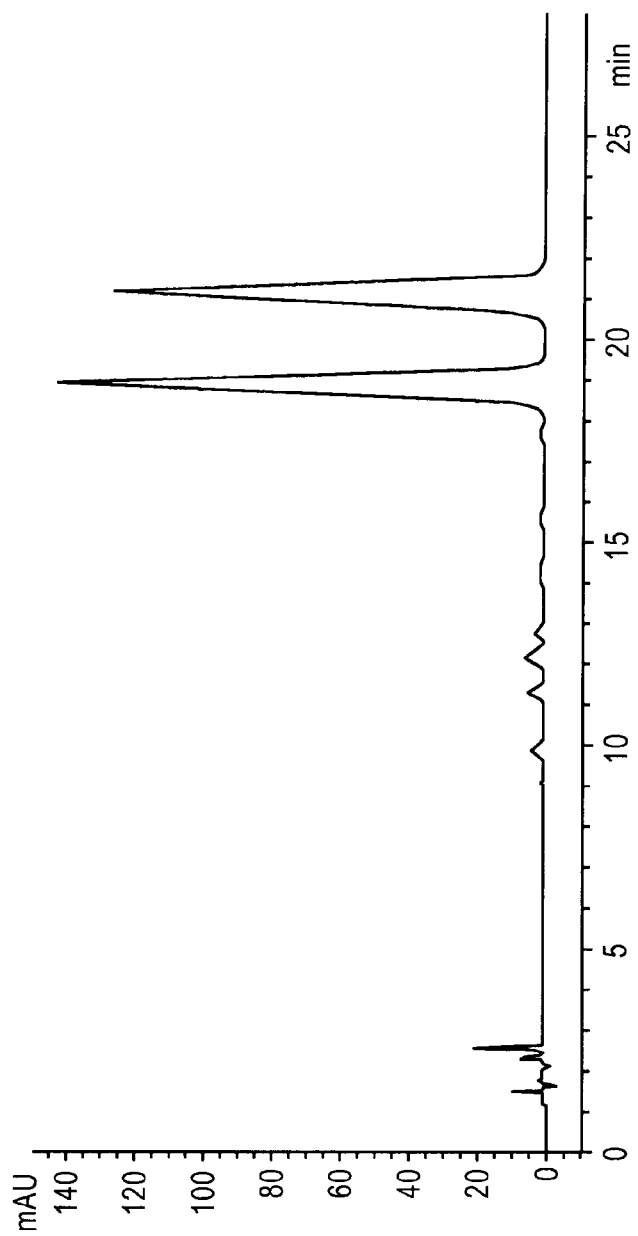
FIGS. 1-8 are graphs relating the examples.

Experimental conditions: column dimension 150×4 mm I.D., particle size 5 µm, temperature 2500, flow rate 1.0 ml/min, detection 240 nm, mobile phase 50 mM formic acid and 25 mM diethylamine in acetonitrile/methanol 9/1 (v/v). See FIG. 1.

Figure 2:
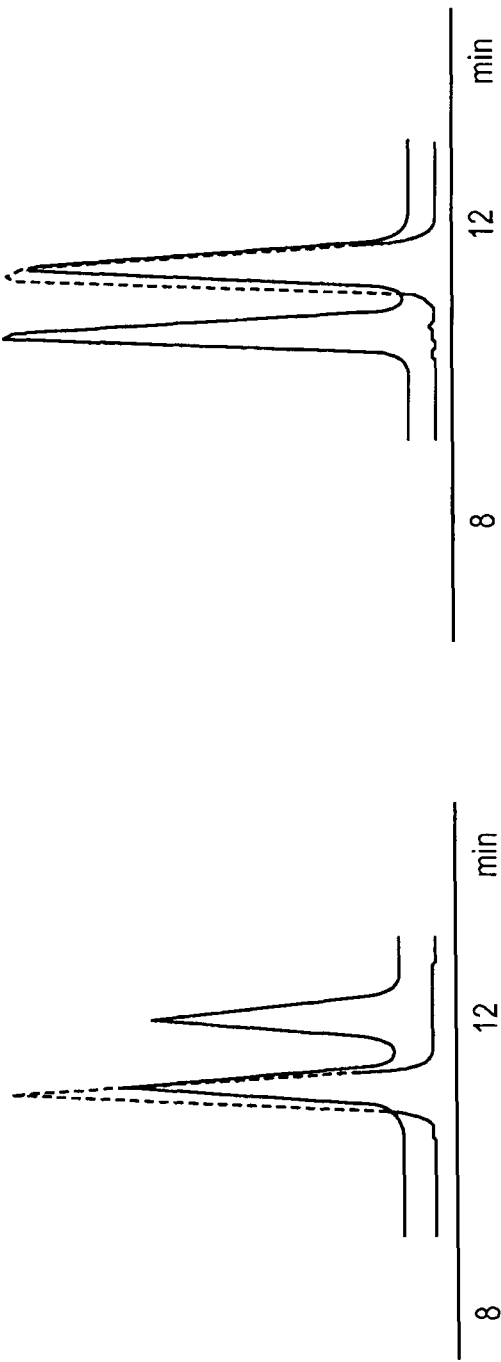

The elution sequence can be reversed by changing to the ion-exchanger material having absolute enantiomeric configuration. See FIG. 2.

left: ion-exchanger material having (1R,2R)-configuration shown above right: ion-exchanger material having (1S,2S)-configuration shown above continuous line: separation of the racemate, dashed line: elution of an individual enantiomer Experimental conditions: column dimension 100×4 mm I.D., particle size 5 μm, temperature 25° C., flow rate 1.0 ml/min, detection 240 nm, mobile phase: 10 mM $NH_4Cl$ in methanol

EXAMPLE 2

Figure 3:
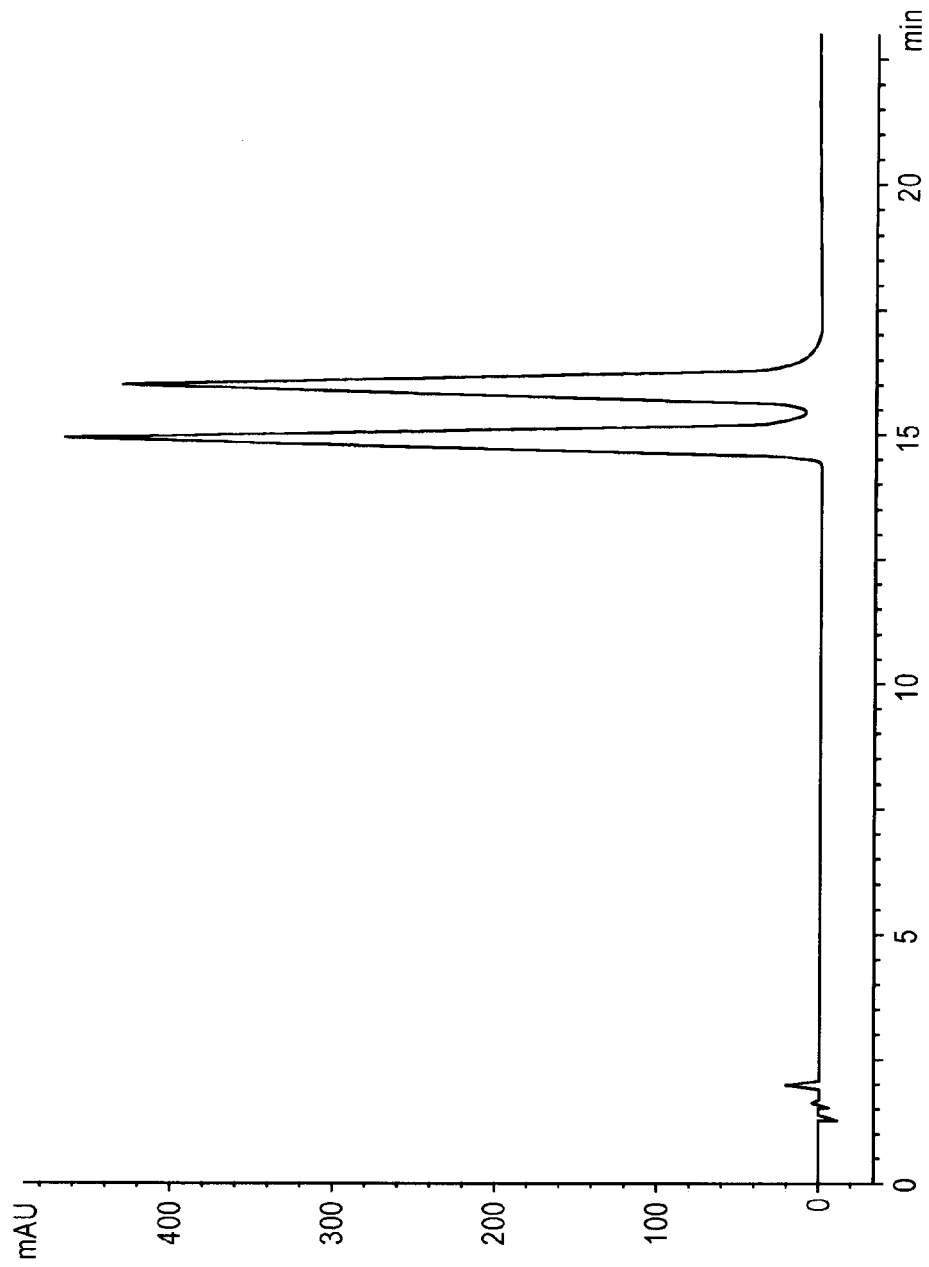
Figure 4:
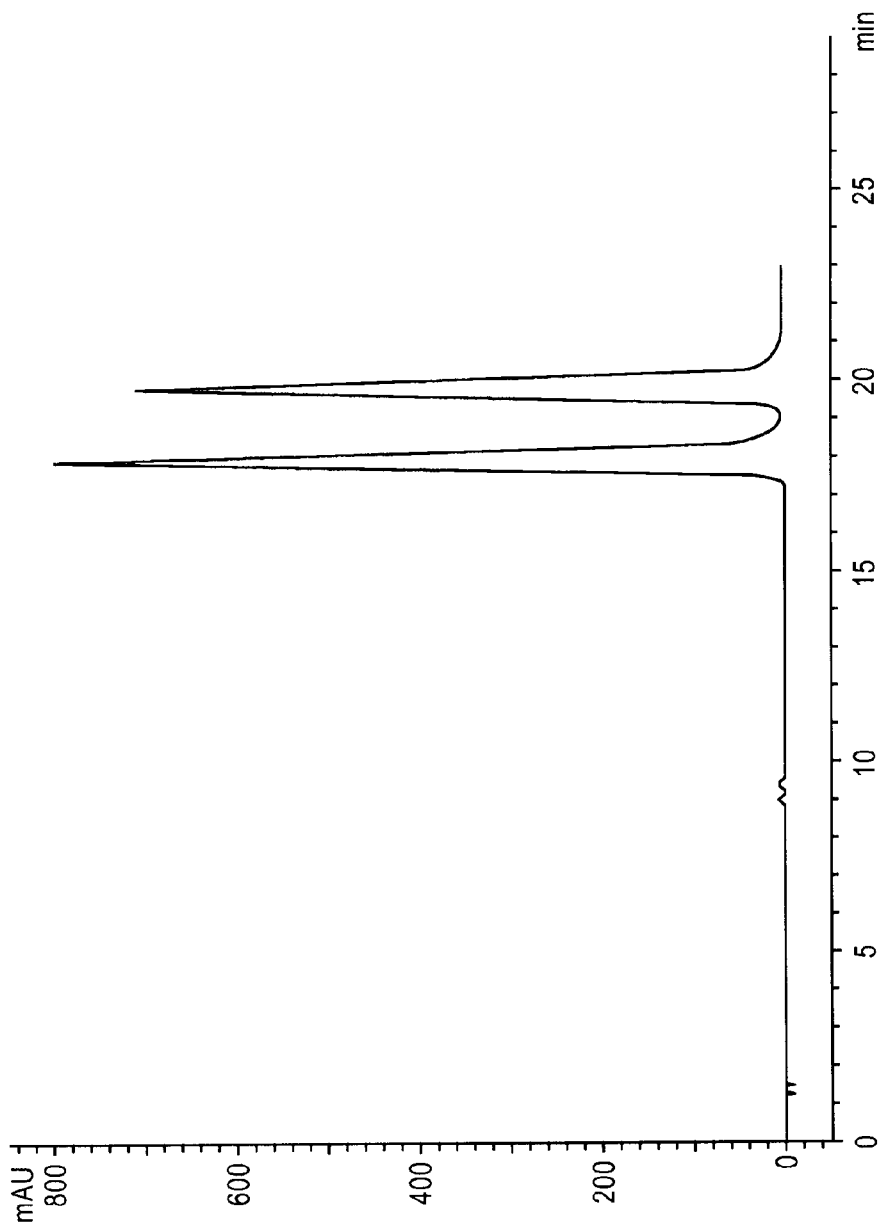

Further examples of the method according to the invention by means of the above-mentioned ion-exchanger material for separation of the racemate of the compound of the formula I in which in a)
$R^1$ denotes allyl,
$R^2$ denotes methyl,
$R^3$, $R^4$ denote H,
$R^5$ denotes H,
$R^6$ denotes methyl
and in b)
$R^1$, $R^2$ denote methyl,
$R^3$, denotes allyl,
$R^4$ denotes H,
$R^5$ denotes H,
$R^6$ denotes methyl:
See FIGS. 3 and 4.

Experimental conditions: column dimension 150×4 mm I.D., particle size 5 μm, temperature 25° C., flow rate 1.0 ml/min, detection 240 nm, mobile phase: 50 mM formic acid and 25 mM diethylamine in methanol.

EXAMPLE 3

Further examples of the method according to the invention by means of zwitterionic ion-exchanger material having the chemical structure

Figure 5:
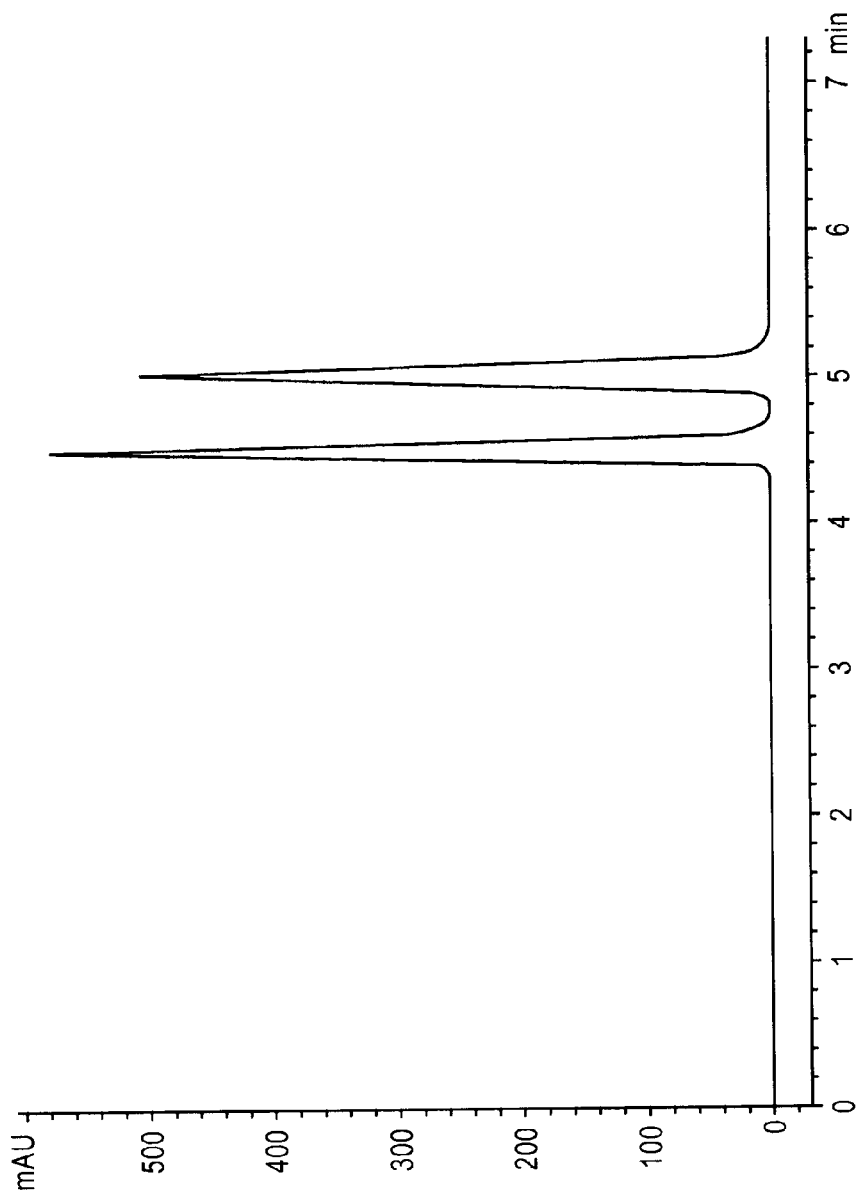
Figure 6:
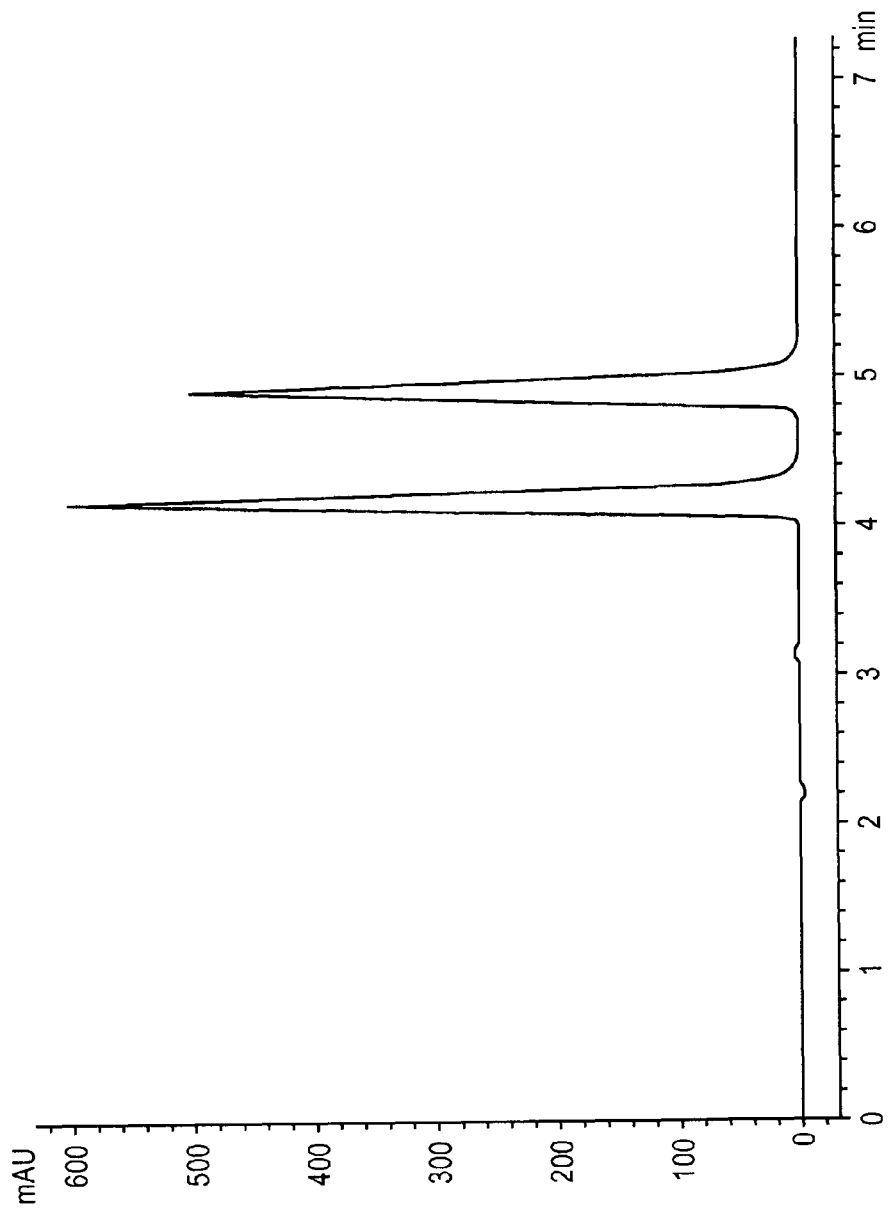

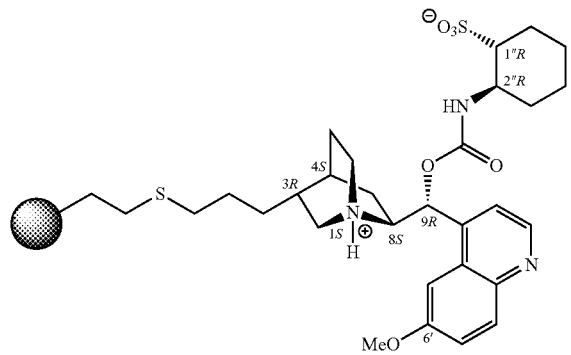

for separation of the racemate of the compound of the formula I in which in
a)
$R^1$, $R^2$ denote methyl,
$R^3$, $R^4$ denote H,
$R^5$ denotes H,
$R^6$ denotes methyl and in b)
$R^1$, $R^2$ denote methyl,
$R^3$, denotes allyl,
$R^4$ denotes H,
$R^5$ denotes H,
$R^6$ denotes methyl:
See FIGS. 5 and 6.

Experimental conditions: column dimension 150×4 mm I.D., particle size 5 μm, temperature 25° C., flow rate 1.0 ml/min, detection 240 nm, mobile phase: 50 mM acetic acid and 25 mM ammonia in methanol.

EXAMPLE 4

Example of the method according to the invention for the preparative separation of the racemate of the compound of the formula I in which
$R^1$ denotes allyl,
$R^2$ denotes methyl,
$R^3$, $R^4$ denote H,
$R^5$ denotes H,
$R^6$ denotes methyl,
using the chiral ion-exchanger material of the following chemical structure, based on silica gel as support material; the type of counterion $X^-$ at the cation exchanger site depends on the type of buffer salt in the mobile phase.

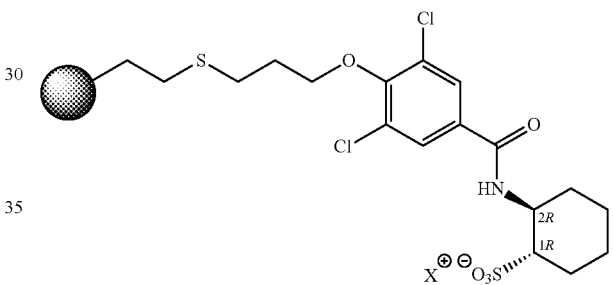

Experimental conditions for the following chromatogram: column dimension 150×4 mm I.D., particle size 5 μm, temperature 25° C., flow rate 1.0 ml/min, detection 254 nm (continuous line), 280 nm (dashed line), mobile phase: 50 mM acetic acid and 25 mM ammonia in acetonitrile/methanol 4/1 (v/v), sample concentration 113 mg/ml, injection volume 26.5 μl.

Figure 7:
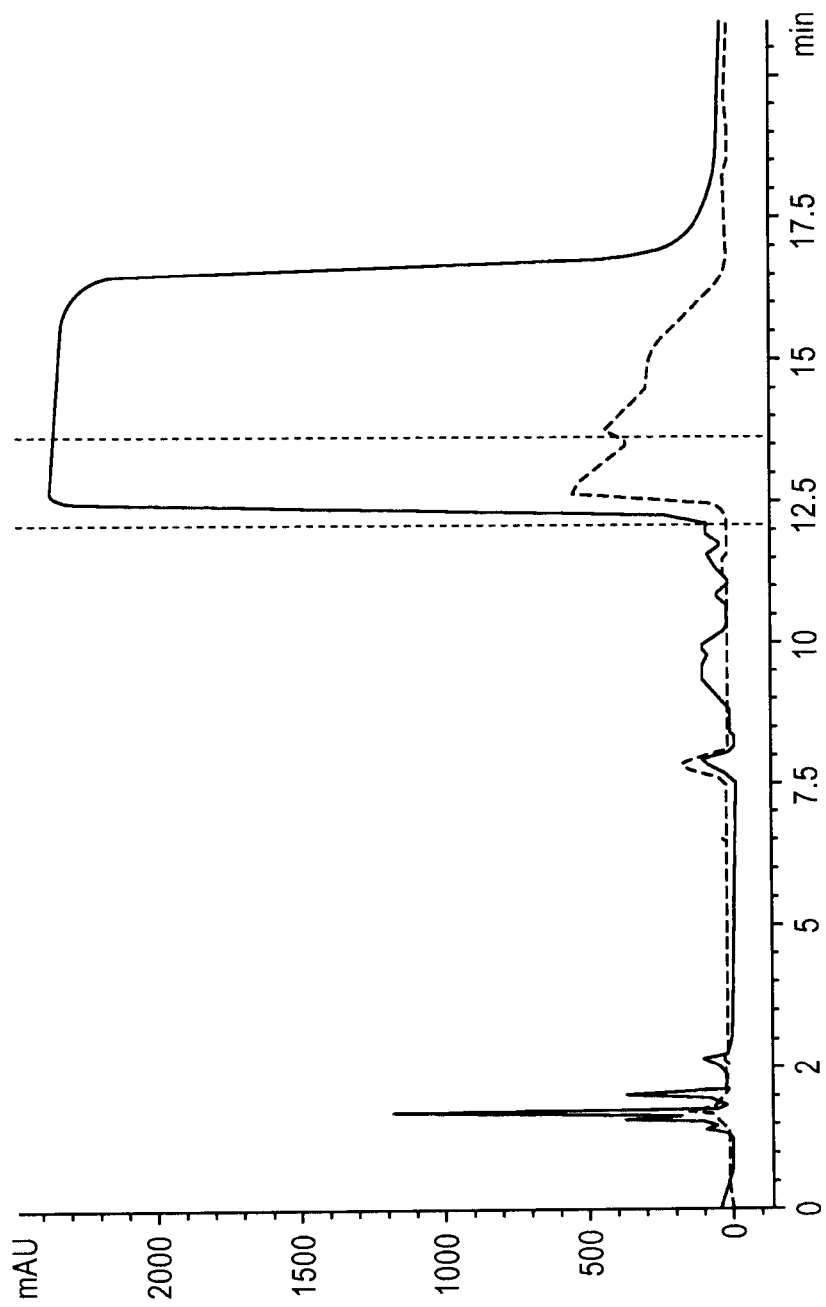

See FIG. 7.

The collected fraction (12.20-13.85 min) for the enantiomer eluted first is indicated in time by the dotted vertical lines.

The enantiomeric purity of the collected fraction can be determined by analysis on the chiral ion-exchanger material.

Experimental conditions for the following chromatogram: absolute configuration of the ion-exchanger material (1S,2S), column dimension 150×4 mm I.D., particle size 5 μm, temperature 25° C., flow rate 1.0 ml/min, detection 254 nm, mobile phase: 50 mM acetic acid and 25 mM ammonia in methanol.

continuous line: analysis of the collected fraction at >98% ee with a yield of >80%, based on the enantiomerdashed line: separation of the corresponding racemate for comparison.

Figure 8:
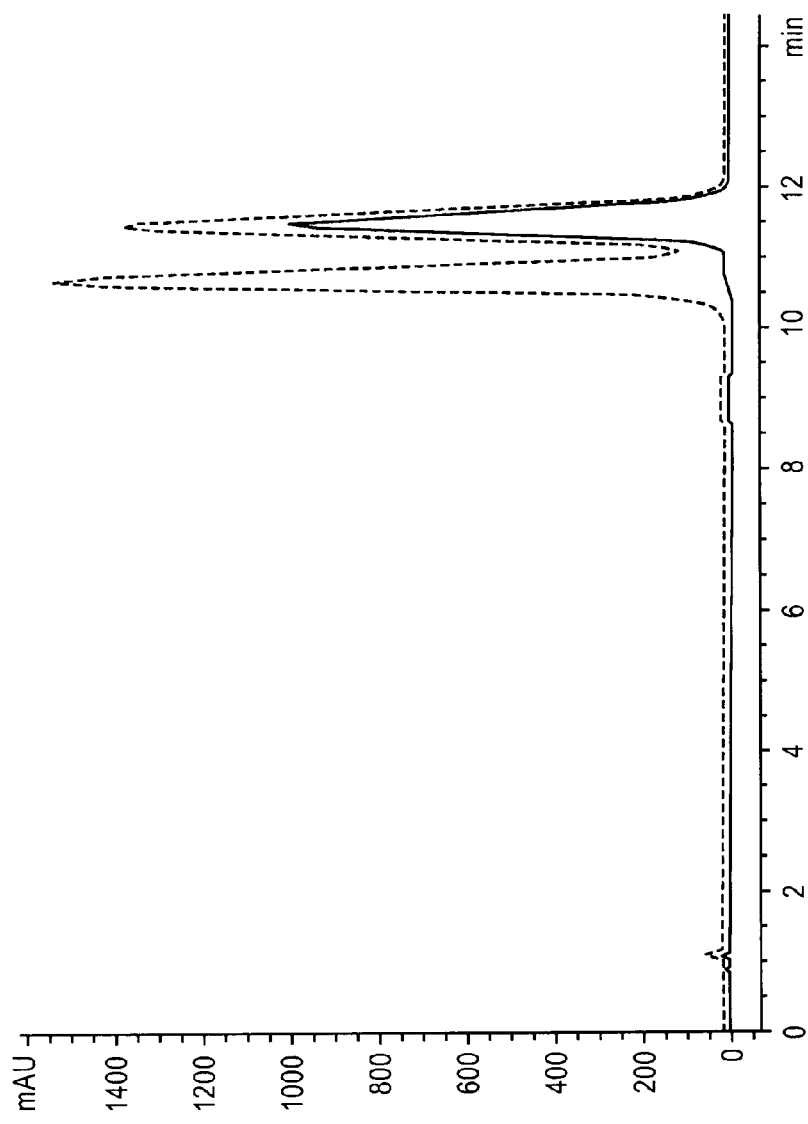

See FIG. 8.

EXAMPLE 5

Examples of chiral compounds which allow the separation of racemates of the compounds of the formula I, for example in dissolved form as addition to the background electrolyte in capillary electrophoresis, can have the following structures:

| Chemical structure | Enantio-selectivity |
|---|---|
| (3,5-dinitrobenzoyl-cyclohexyl-SO₃⁻) | 1.075 |
| (3,5-dichloro-4-allyloxybenzoyl-cyclohexyl-SO₃⁻) | 1.030 |
| (3,5-dichloro-4-allyloxybenzoyl-cyclohexyl-COO⁻) | 1.015 |
| (3,5-dinitrobenzoyl-cyclohexyl-COO⁻) | 1.028 |
| (3,5-dichloro-4-allyloxybenzoyl-cyclohexyl-COO⁻) | 1.006 |
| (3,5-dinitrobenzyloxycarbonyl-cyclohexyl-SO₃⁻) | 1.012 |
| (3,5-dichlorophenylurea-cyclohexyl-SO₃⁻) | 1.033 |
| (1-naphthylurea-cyclohexyl-SO₃⁻) | 1.024 |
| (3,5-dinitrobenzoyl-tert-leucinol-SO₃⁻) | 1.046 |
| (BINOL phosphate) | 1.037 |

Experimental conditions of the reciprocal CE experiment: background electrolyte: 50 mM formic acid+25 mM triethylamine+50 mM 4-amino-3,6-dihydro-2-dimethylamino-6-methyl-1,3,5-triazine (enantiomerically pure) in ethanol; T=25° C.; injection: 50 mbar/5 s; samples: compounds from the table in racemic form (1-10 mg/ml in electrolyte); fused silica capillaries: 50 μm internal diameter; total length=50 cm; effective length to the detector=41.5 cm; voltage=−25 kV; after 30 minutes, a pressure of 20 mbar is applied to the injector side in order to remove non-eluted compounds from the capillary.

After suitable anchoring of these compounds to a support, such as particulate or monolithic silica gel, or particulate or monolithic organic polymers, ion exchangers which enable the separation of the chiral compounds of the formula I into their enantiomers can be obtained.

The invention claimed is:

1. A method for the chromatographic separation of the enantiomers of a compound of the formula I or an acid-addition salt thereof, wherein said separation of the enantiomers is carried out on a chiral ion exchanger material

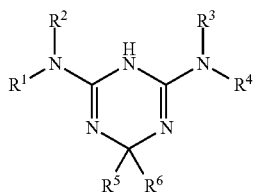
I wherein
R$^1$ and R$^2$ are A;
R$^3$ and R$^4$ are H;
R$^5$ is H,
R$^6$ is A,
A is unbranched or branched alkyl having 1-10 C atoms, wherein 1-7 H atoms may be replaced by F, or cyclic alkyl having 3-7 C atoms;
and
comprising separating the enantiomers on a chiral ion exchanger which is
a) of the structure below wherein X is a counterion determined by the type of buffer salt in the mobile phase and the sphere represents a support,

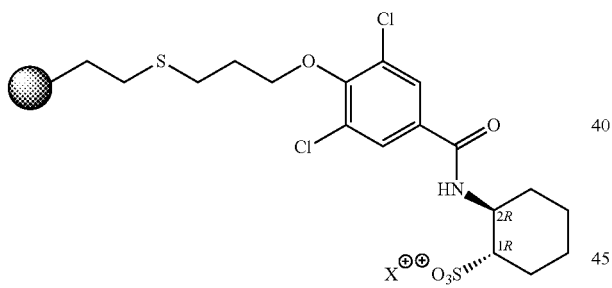

b) of the structure below where the sphere represents a support:

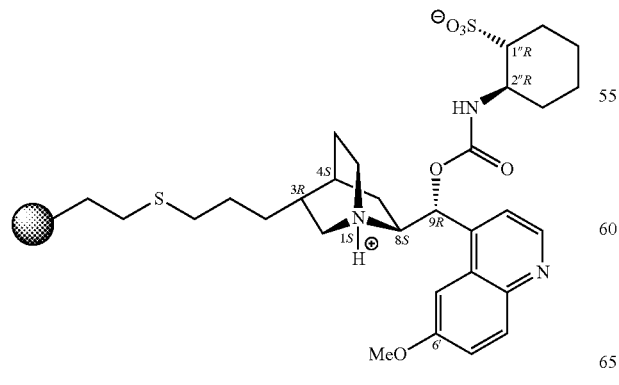

or
c) contains one of the following structures, a spacer and a support,

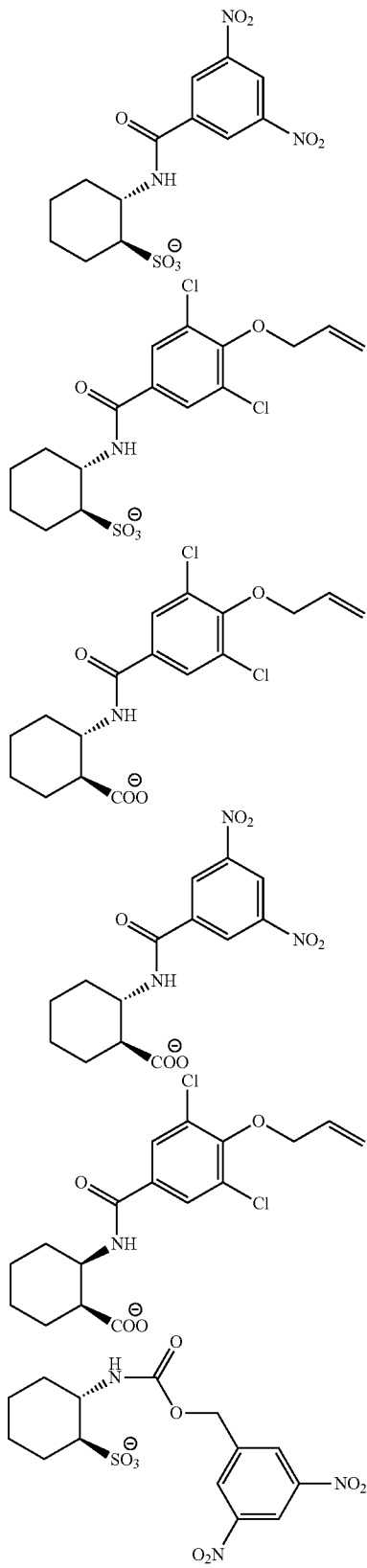

-continued

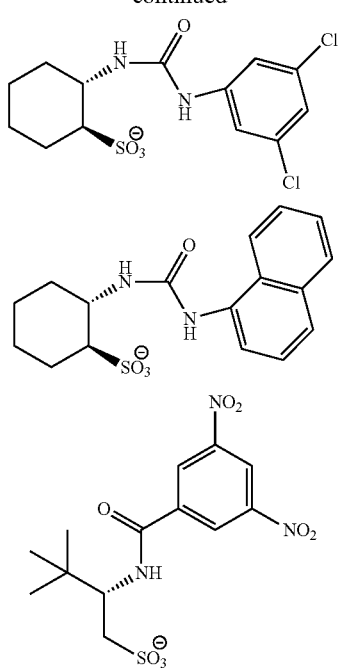

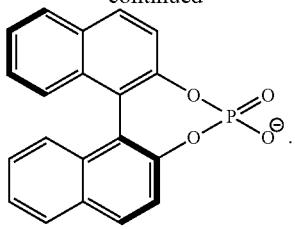

2. The method of claim 1, wherein $R^1$, $R^2$ are methyl, and $R^6$ is methyl.

3. The method of claim 1, wherein an eluent is used in the separation wherein the eluent comprises
   i) an organic solvent from the group methanol, ethanol, propanol, acetonitrile, THF, dioxane, ethyl acetate, chloroform, dichloromethane, tert-butyl methyl ether, hexane, heptane, or a binary, ternary, quaternary mixture of these solvents with addition of co- and counterions or also without ionogenic additives,
   ii) an aqueous medium with or without addition of buffers and with or without miscible polar organic solvents from the group as specified under i.),
   iii) supercritical or subcritical $CO_2$ with or without an organic solvent as specified under i.), with addition of co- and counterions or also without ionogenic additives.

* * * * *